United States Patent
Kerr (10) Patent No.: US 7,105,017 B2
(45) Date of Patent: Sep. 12, 2006

(54) AXIALLY-CONNECTED STENT/GRAFT ASSEMBLY

(76) Inventor: Andrew Kerr, 440 Riverside Dr., New York, NY (US) 10027

( * ) Notice: Subject to any disclaimer, the term of this patent is extended or adjusted under 35 U.S.C. 154(b) by 229 days.

(21) Appl. No.: 09/900,241

(22) Filed: Jul. 6, 2001

(65) Prior Publication Data
US 2002/0151957 A1    Oct. 17, 2002

Related U.S. Application Data

(60) Provisional application No. 60/283,108, filed on Apr. 11, 2001.

(51) Int. Cl.
*A61F 2/06* (2006.01)
(52) U.S. Cl. ..................... 623/1.13; 623/1.16
(58) Field of Classification Search ............... 623/1.13, 623/1.16; 606/153, 155
See application file for complete search history.

(56) References Cited

U.S. PATENT DOCUMENTS

| | | | |
|---|---|---|---|
| 5,064,435 A * | 11/1991 | Porter .......................... | 623/12 |
| 5,078,726 A | 1/1992 | Kreamer | |
| 5,316,023 A | 5/1994 | Palmaz et al. | |
| 5,578,072 A * | 11/1996 | Barone et al. ............. | 623/1.13 |
| 5,591,195 A | 1/1997 | Taheri et al. | |
| 5,693,088 A | 12/1997 | Lazarus | |
| 5,728,131 A | 3/1998 | Frantzen et al. | |
| 5,769,887 A | 6/1998 | Brown et al. | |
| 5,800,526 A * | 9/1998 | Anderson et al. .......... | 623/1.13 |
| 5,817,126 A * | 10/1998 | Imran ....................... | 623/1.15 |
| 5,824,037 A * | 10/1998 | Fogarty et al. ............ | 623/1.13 |
| 5,928,281 A * | 7/1999 | Huynh et al. .............. | 623/2.14 |
| 6,015,422 A | 1/2000 | Kerr | |
| 6,102,918 A | 8/2000 | Kerr | |
| 6,110,198 A | 8/2000 | Fogoarty et al. | |
| 6,152,956 A * | 11/2000 | Pierce ....................... | 623/1.13 |
| 6,168,620 B1 | 1/2001 | Kerr | |
| 6,273,909 B1 * | 8/2001 | Kugler et al. .............. | 623/1.13 |
| 6,290,720 B1 * | 9/2001 | Khosravi et al. .......... | 623/1.13 |

(Continued)

FOREIGN PATENT DOCUMENTS

EP    0 732 089    9/1996

(Continued)

OTHER PUBLICATIONS

"The Complete Illustrated Guide to Joinery" by Gary Rogowski, Section 10 Butt Joints.

(Continued)

*Primary Examiner*—David H. Willse
*Assistant Examiner*—Javier G. Blanco
(74) *Attorney, Agent, or Firm*—Gerald E. Hespos; Anthony J. Casella (57) ABSTRACT

A stent/graft assembly includes a tubular graft having an upstream end, a downstream end and a tubular passage between the ends. The assembly also includes a tubular stent having an upstream end, a downstream end and a tubular passage. The upstream end of the tubular graft is affixed in substantially end-to-end relationship with the downstream end of the tubular stent. The affixation may employ sutures, bonding, hooks or the like. The end-to-end connection may also require a slight overlapping to ensure an adequate affixation. The end-to-end disposition of the tubular graft and tubular stent reduces the cross-sectional profile of the stent/graft assembly. One or more wires may extend from the tubular stent through the tubular graft for anchoring near the downstream end of the tubular graft. The wire prevents axial collapsing of the tubular graft and provide radial support for the tubular graft.

2 Claims, 12 Drawing Sheets

U.S. PATENT DOCUMENTS

| | | | |
|---|---|---|---|
| 6,383,171 B1 * | 5/2002 | Gifford et al. | 604/508 |
| 6,409,757 B1 * | 6/2002 | Trout, III et al. | 623/1.36 |
| 6,565,599 B1 * | 5/2003 | Hong et al. | 623/1.15 |
| 6,602,280 B1 * | 8/2003 | Chobotov | 623/1.11 |
| 6,712,843 B1 * | 3/2004 | Elliott | 623/1.15 |
| 6,749,628 B1 | 6/2004 | Callol et al. | |

FOREIGN PATENT DOCUMENTS

| | | |
|---|---|---|
| EP | 0 809 980 | 12/1997 |
| FR | 2765097 A1 * | 12/1998 |
| WO | WO 9847447 A1 * | 10/1998 |
| WO | WO 01/56501 A1 * | 8/2001 |

OTHER PUBLICATIONS

"Butt joint versus belleved gold margin in metal-ceramic crowns" J.W. McLean and A.D. Wilson.

Fundametals of Fixed Prosthodontics "Chapter 9 Principles of Tooth Preparations" pp. 119-131.

"Cabinetmaking and Millwork" John L. Feirer.

The American Heritage Dictionary of the English Language: Fourth Edition. 2000.

ArtLex Art Dictionary.

GetWoodworking.com.

Vormann.com; and.

Wowimadeit.com.

* cited by examiner

AXIALLY-CONNECTED STENT/GRAFT ASSEMBLY

This application claims the benefit of provisional application No. 60/283,108 filed Apr. 11, 2001.

BACKGROUND OF THE INVENTION

1. Field of the Invention

The subject invention relates to a stent and graft assembly for treating vascular anomalies, such as aneurysms.

2. Description of the Related Art

Vascular anomalies are considered to include blood vessels that are damaged, weakened or otherwise impaired. The anomaly may include a local change in the cross-sectional dimensions of the blood vessel. For example, aneurysms include a local area where a blood vessel expands to a larger cross-sectional area due to disease, weakening or other damage.

The abdominal aorta extends from the heart and through the abdomen. The abdominal aorta then feeds abdominal organs and the right and left iliac arteries that bring blood to the right and left legs respectively. The aorta is prone to aneurysms. Abdominal aortic aneurysms that are not treated in a timely manner can lead to rupture, detachable, infection or the production of emboli which can flow downstream and clot a smaller blood vessel. A ruptured abdominal aortic aneurysm typically is fatal due to a loss of the large volume of blood that flows through the abdominal aorta.

Aneurysms can be corrected by grafts. The typical graft is implanted surgically by accessing the site of the aneurysm, cutting open the aneurysm and then surgically forming an appropriate fabric into a tubular shape that spans the aneurysm. Thus, upstream and downstream ends of the prior art graft are sutured to healthier regions of the blood vessel.

The prior art also includes endovascular grafts. An endovascular graft comprises a flexible tubular member formed from a synthetic fabric. The graft is selected to have an outside cross-sectional dimension that approximates the inside cross-sectional dimensions of the blood vessel on either side of the aneurysm. The graft also is selected to have a length that exceeds the length of the damaged area of the blood vessel. An unsupported flexible tubular graft has a tendency to collapse in the presence of the flowing blood and could be transported downstream by the blood flow. As a result, endovascular grafts are used in combination with a stent. Stents take many forms, including balloon expandable stents and self-expanding stents, but typically are resilient cylindrical members that are inserted axially through the tubular graft prior to insertion into the blood vessel. The stent and the graft are sutured together prior to deployment so that the opposed ends of the stent align with the opposed ends of the graft. The endovascular graft assembly then is inserted through a healthy region of the blood vessel and is advanced through the circulatory system to the aneurysm or other damaged region of the blood vessel. More particularly, the endovascular graft assembly is advanced to a position where the endovascular graft assembly bridges the aneurysm or other damaged portion of the blood vessel. However, the opposed axial ends of the endovascular graft assembly extend beyond the aneurysm. The stent then is expanded to hold the graft in an expanded tubular condition with at least the opposed axial end regions of the graft being urged tightly against the interior of healthy regions of the blood vessel. The stent and the graft of the prior art endovascular graft assembly are coaxial, and longitudinally coextensive.

Prior art assemblies of stents and grafts typically perform well. However, the coaxially and longitudinally coextensive arrangement of the stent and graft has resulted in a cross-sectionally large assembly. A cross-sectionally large graft and stent assembly can be difficult to insert and deliver intravascularly to the damaged section of the blood vessel and may require surgery.

The inventor herein has developed low-profile stent/graft structures, as shown for example in U.S. Pat. No. 6,015,422, U.S. Pat. No. 6,102,918 and U.S. Pat. No. 6,168,620.

In view of the above, it is an object of the subject invention to provide improvements in vascular stent and graft assemblies that provide a small cross-section and low profile.

It is also an object of the invention to provide an endovascular stent and graft assembly that can be introduced easily into and through the damaged or diseased section of a blood vessel.

A further object of the subject invention is to provide a system of endovascular stents and grafts that can be assembled intravascularly through damaged regions of a blood vessel.

Another object of the invention is to provide an endovascular stent/graft assembly that prevents migration of the assembly after deployment.

An additional object of the invention is to provide an endovascular stent/graft assembly for treating patients with short and/or angulated vascular necks adjacent an aneurysm.

Yet another object of the invention is to provide a system of endovascular grafts and stents that will prevent an aneurysm from filling with blood that flows into the aneurysm from small side blood vessels.

SUMMARY OF THE INVENTION

The subject invention is directed to an endovascular graft assembly that comprises at least one tubular vascular graft and at least one fixation device. The tubular graft and the fixation device are connected substantially in end-to-end relationship with little or no longitudinal overlap. The tubular graft has a length that exceeds the length of a damaged section of a blood vessel that is being repaired by the endovascular graft assembly. The tubular graft also has a cross-sectional size that is about 10%–30% wider than the cross-sectional size of the blood vessel that is being repaired. The tubular graft preferably is formed from a synthetic material, such as a material formed from an ultra thin polyester fiber, or other vascular graft materials known to those skilled in this art.

The fixation device may comprise a generally tubular stent. One end of the tubular stent is securely affixed to one end of the tubular graft. The end-to-end fixation of the graft to the stent preferably is carried out with little or no telescoping between the tubular graft and the stent. However, a slight amount of telescoping (e.g. 0–20 mm) may be required to ensure a secure and substantially permanent interengagement. The connection between the tubular graft and the tubular stent may be achieved by hooking, stitching, fusing or other such secure connection techniques. The connection need not be continuous around the peripheries of the stent and the tubular graft. Thus, the stent and the tubular graft merely may be connected at one location on their respective ends or at plural spaced-apart locations.

The fixation device need not be a tubular stent. Rather, the fixation device may comprise a plurality of hooks that extend from at least one longitudinal end of the tubular graft. The hooks can be engaged with healthy sections of blood vessel on either side of an aneurysm. The fixation device may further include an annular ring affixed to an axial end of the tubular graft, and the hooks may project axially from the ring. The ring functions to keep the tubular graft open during insertion of the endovascular graft assembly into the blood vessel.

The endovascular graft assembly further comprises an internal stent to provide radial support for the tubular graft of the endovascular graft assembly. However, unlike prior art endovascular graft assemblies, the internal stent of the subject invention is deployed after the end-to-end assembly of the fixation device and tubular graft have been positioned properly across the aneurysm. The internal stent may be a balloon expandable stent or a self-expanding stent. However, the insertion of the internal stent after the insertion of the end-to-end assembly of the fixation device and tubular graft greatly facilitates the deployment of the entire endovascular stent/graft assembly to the proper location.

The endovascular graft assembly may further include at least one support that extends from the fixation device into the graft to prevent the graft from collapsing radially or axially during or after installation and/or to provide radially outward support for the graft. The support may comprise at least one longitudinally extending wire extending from the fixation device substantially entirely through the graft and then anchored at the axial end of the graft opposite the stent. The support may alternatively comprise a coil extending substantially from the fixation device, through the graft and to the end of the graft opposite the fixation device. The support may be connected to the fixation device or unitary with portions of the fixation device.

The endovascular graft assembly may comprise at least two fixation devices connected respectively to opposite ends of a tubular graft. The endovascular graft assembly may further comprise a plurality of tubular grafts connected respectively to opposite axial ends of fixation devices. The tubular graft and tubular fixation devices need not be all of identical cross-sectional sizes. Additionally, the assembly may comprise plural fixation devices connected axially to the legs or branches of a bifurcated or trifurcated graft, such as a graft having an inverted Y-shape. Furthermore, certain components of the assembly may be assembled intravascularly and intraoperatively.

DETAILED DESCRIPTION OF THE PREFERRED EMBODIMENTS

Figure 1:
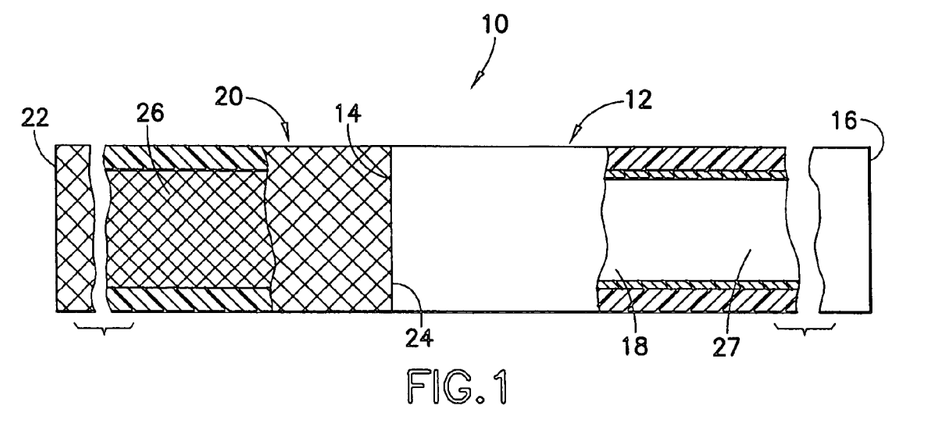
FIG. 1 is an elevational, partly in section, view of an endovascular stent/graft assembly in accordance with a first embodiment of the invention.

An endovascular stent/graft assembly in accordance with a first embodiment of the invention is identified generally by the numeral 10 in FIG. 1. The endovascular stent/graft assembly 10 includes a substantially tubular graft 12 having a flexible wall formed from a synthetic material, such as a polyester material that is substantially impervious to fluid transmission or that becomes substantially impervious after exposure to blood. The tubular graft 12 has an upstream end 14, a downstream end 16 and a fluid passage 18 extending between the ends. The endovascular stent/graft assembly 10 further comprises a tubular stent 20 having an upstream end 22, a downstream end 24 and a passage 26 extending between the ends. The tubular stent 20 may be of known construction and may be formed from materials that are known to those skilled in the art of treating vascular anomalies with endovascular stent/graft assemblies, such as polyethylene terepthalate and PTFE, including materials sold under the trademarks DACRON® and GORTEX®.

The terms upstream and downstream used to define the ends of the tubular graft 12 and the tubular stent 20 are employed with reference to the direction of blood flow existing during insertion of a stent graft assembly 10. More particularly, the endovascular stent/graft assembly preferably will be inserted into a blood vessel such that the tubular stent 20 is upstream and facing into the flow of blood. The tubular graft 12 then will trail behind the stent relative to the direction of insertion of the endovascular stents/graft assembly 10 and relative to the direction of the blood flow. This preferred orientation of the endovascular stent/graft assembly 10 will enable the much more flexible tubular graft 12 to perform much in the nature of a wind-sock that is urged into an extended condition by forces exerted by the blood flow. A reversed insertion, of this first embodiment, on the other hand, could cause the flexible tubular graft 12 to collapse in response to the blood flow.

Figure 2:
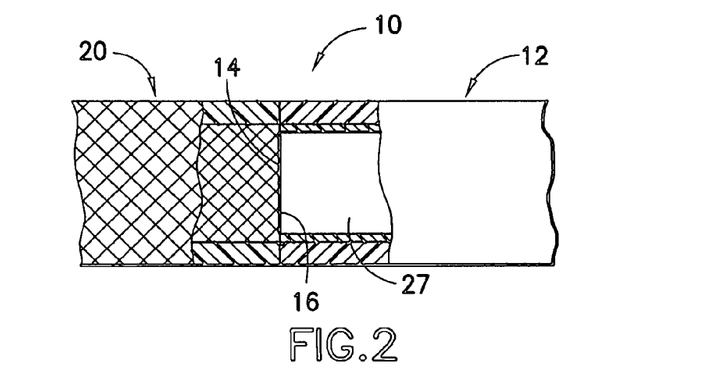
FIG. 2 is an enlarged elevational view, partly in section, of a connection between the stent and graft of the assembly in either FIG. 1.
Figure 3:
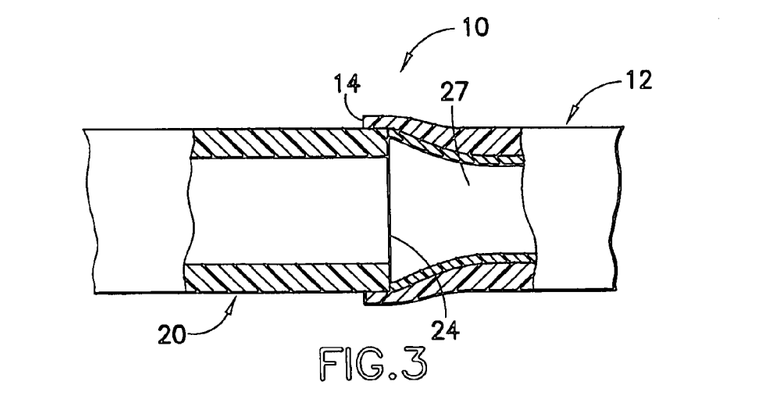
FIG. 3 is an enlarged elevational view partly in section, similar to FIG. 2, but showing an alternate connection between the stent and graft.

As shown generally in FIG. 1 and more specifically in FIGS. 2 and 3, the tubular graft 12 and the tubular stent 20 are connected substantially in end-to-end axial relationship. More particularly, as shown in FIG. 2, the upstream end 14 of the tubular graft 12 is butted against the downstream end 24 of the tubular stent 20 to achieve a true end-to-end axial connection between the tubular graft 12 and the tubular stent 20. This pure axial end-to-end abutment can be achieved by fusing, suturing or other known connection means that will be appreciated by persons skilled in this art.

The true end-to-end axial connection may be difficult to achieve with certain material employed for the tubular graft and the tubular stent. In these situations, a substantially end-to-end axial connection can be achieved with a slight telescoping overlap as shown schematically in FIG. 3. With this optional arrangement, the inner circumferential surface of the tubular graft 12 adjacent the upstream end 14 may be telescoped slightly over the outer circumferential surface of the tubular stent 20 adjacent the downstream end 24. Sutures, fusing or other known connections then may be employed to permanently affix the slightly overlapped ends of the tubular graft 12 and the tubular stent 20.

FIGS. 2 and 3 depict substantially continuous connection between the annular periphery at the upstream end of the tubular graft 12 and the annular periphery at the downstream end 24 of the tubular stent 20. However, such a continuous connection may not be required in many situations. Rather, one or more points of contact and affixation may be sufficient between the upstream end 14 of the tubular graft 12 and the downstream end of the tubular stent 20.

The endovascular stent/graft assembly 12 further comprises an internal stent 27 that is deployed after the end-to-end connected tubular graft 12 and tubular stent 20 are in place. The internal stent 27 may be a balloon expandable stent or a self-expanding stent and functions to maintain tubular graft 12 in an expanded non-occluded condition. Furthermore, the internal stent 27 maintains outer circumferential surface regions of the tubular graft 12 near the upstream and downstream ends 14 and 16 in face-to-face engagement with the inner surface of the blood vessel upstream and downstream from the aneurysm. The insertion of the internal stent 27 after positioning the tubular graft 12 and the tubular stent 20 is considerably easier than the prior art endovascular grafts that simultaneously attempt to advance a coaxial arrangement of graft and stent that are longitudinally coextensive with one another.

Figure 4:
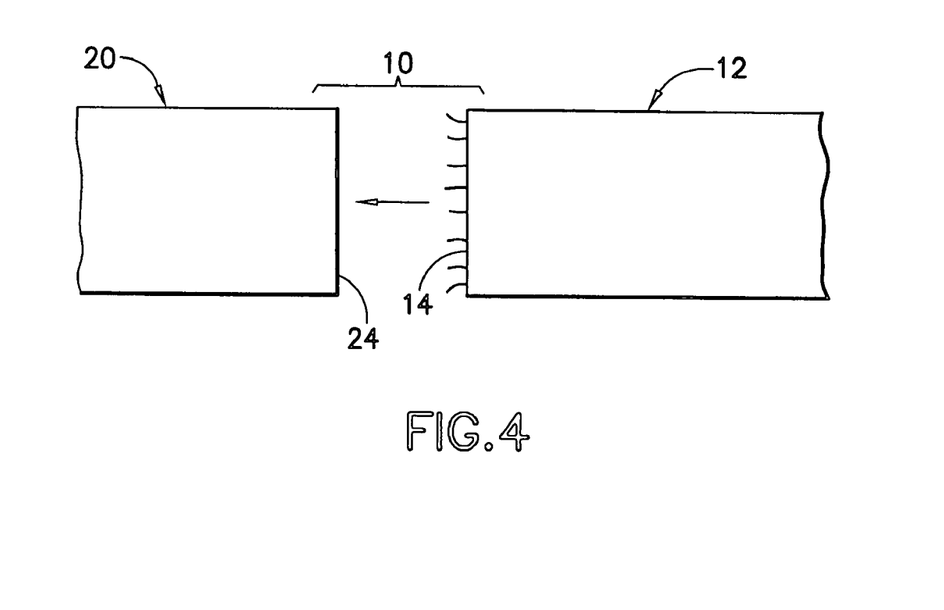
FIG. 4 is an elevational view of the graft with hooks for fixation to the stent or to a blood vessel.
Figure 5:
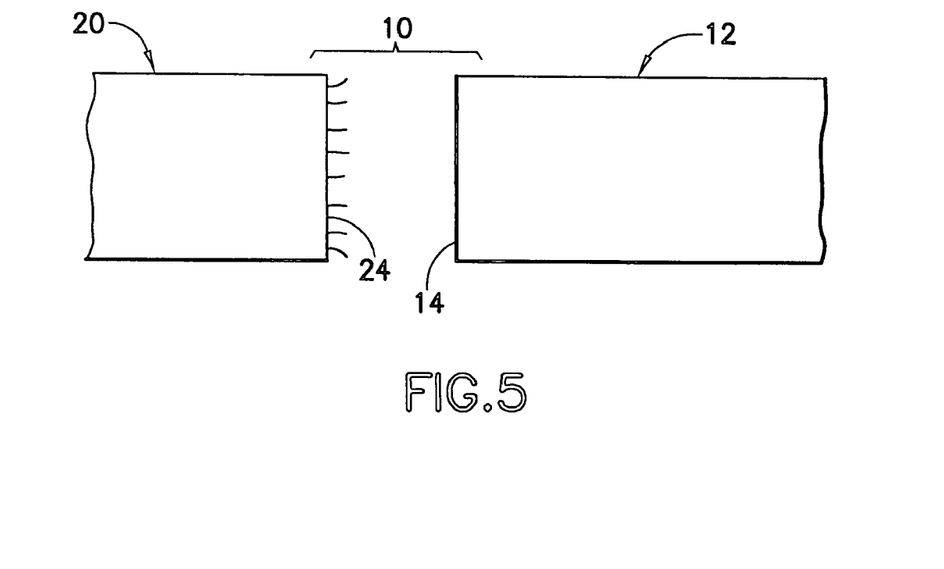
FIG. 5 is an elevational view similar to FIG. 4, but showing hooks on the tubular stent.

An alternate end-to-end connection between the tubular graft 12, as shown in FIG. 4, includes a plurality of hooks 28 woven or otherwise incorporated into the tubular graft 12 to extend axially beyond at least the upstream end 14. The hooks 28 on the upstream end 14 of the tubular graft 12 can be engaged into the circumferential surface of the blood vessel. Thus, the hooks 28 function as a fixation device that is an alternate to the tubular stent 20 shown in FIGS. 1–3. The hooks 28 can be mounted to an annular ring (not shown) that can be affixed to the upstream end 14 of the tubular graft 12. Thus, the combination of the ring and the hooks 28 may function as the fixation device. A variation of the FIG. 4 embodiment, the hooks 28 at the upstream end 14 of the tubular graft 12 can be engaged into portions of the tubular stent 20 adjacent the downstream end 24. Alternatively, as shown in FIG. 5, hooks 30 may extend axially beyond the downstream end 24 of the tubular stent 20 for engagement with portions of the tubular graft 12 adjacent the upstream end 14.

Figure 6:
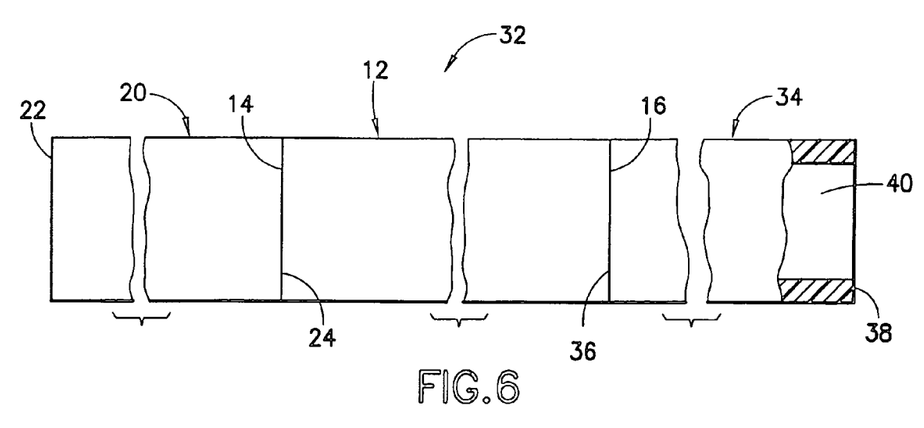
FIG. 6 is an elevational view of an endovascular stent/graft assembly in accordance with a second embodiment of the invention.

FIG. 6 shows an endovascular stent/graft assembly 32 in accordance with a second embodiment of the invention. The endovascular stent/graft assembly 32 includes a tubular graft 12 substantially identical to the tubular graft 12 in the embodiment of FIG. 1. The stent/graft assembly 32 further includes an upstream tubular stent 20 substantially identical to the tubular stent 20 in the embodiment of FIG. 1. However, the stent/graft assembly 32 further includes a downstream stent 34. The downstream stent 34 has an upstream end 36, a downstream end 38 and a tubular passage 40 extending between the ends. The upstream end 36 of the downstream stent 34 is connected in substantially end-to-end relationship with the downstream end 16 of the tubular graft 12 by any of the connection arrangements depicted respectively in FIGS. 2–5. The downstream stent 34 can be connected to the tubular graft prior to insertion of the stent/graft assembly 32 into the blood vessel. Alternatively, the sub-assembly of the tubular graft 12 and the upstream stent 20 can be inserted into the blood vessel substantially as shown in FIG. 1. The downstream stent 34 then can be inserted subsequently and connected intraoperatively to the downstream end 16 of the tubular graft 12.

Figure 7:
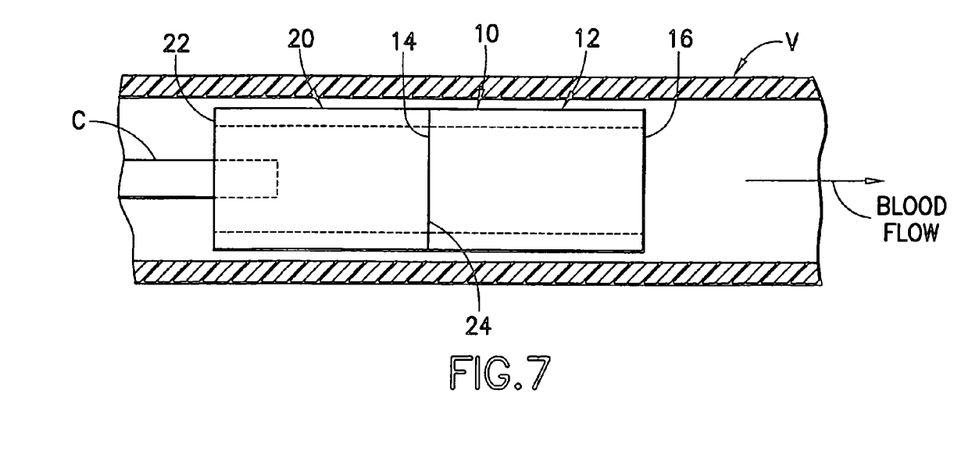
FIG. 7 is a schematic illustration of the endovascular stent/graft assembly of FIG. 1 inserted into a blood vessel.
Figure 8:
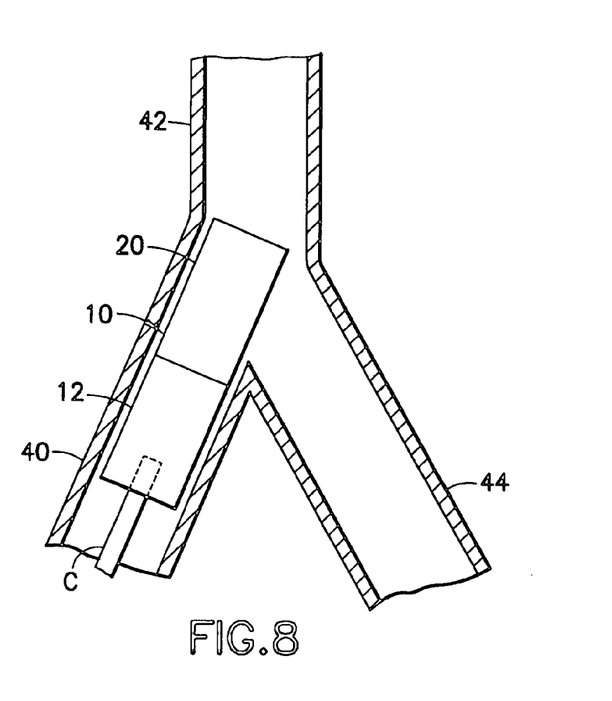
FIG. 8 is a schematic illustration of an insertion of the endovascular stent/graft assembly of FIG. 1 into the abdominal aorta.

As noted above, and as illustrated generally in FIG. 1, the endovascular stent/graft assembly 10 is fixed into the blood vessel with the tubular graft 12 in a downstream position relative to the tubular stent 20. This orientation, does not, however, imply a required direction of insertion. For example, as depicted in FIG. 7, a catheter C is employed to insert the endovascular stent/graft assembly 10 into a blood vessel V along the direction of flow and the tubular graft 12 leading the tubular stent 20. Thus, despite the slow movement of the catheter C and the stent/graft assembly 10 through the blood vessel V in the direction of the blood flow, the tubular graft 12 will extend axially beyond the tubular stent 20 with a substantially wind-sock effect as described above and as shown in FIG. 7. Alternatively, the catheter C can be used to insert the endovascular stent/graft assembly 10 in opposition to the direction of blood flow, but with the tubular stent 20 in the upstream position and leading the endovascular stent/graft assembly 10 into the direction of blood flow. More specifically, FIG. 8 schematically depicts the insertion of the endovascular stent/graft assembly 10 through the right iliac artery 40 and into the abdominal aorta 42, with the tubular stent 20 in the upstream position relative to the tubular graft 12, and with the tubular stent 20 leading the insertion against the direction of blood flow.

Figure 9:
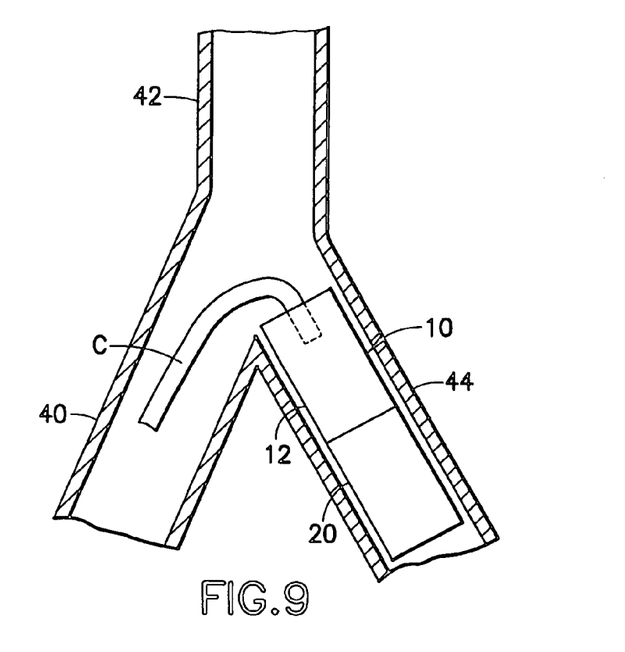
FIG. 9 is a schematic illustration of the endovascular stent/graft assembly of FIG. 1 deployed through the right iliac artery and then inserted into the left iliac artery.

In certain procedures, the stent/graft assembly may start in a direction against the flow of blood but move into a different blood vessel to follow the flow of blood. More particularly, FIG. 9 depicts the insertion of the stent/graft assembly 10 into the right iliac artery 40 for eventual insertion into the left iliac artery 44. The initial part of this insertion will have the endovascular stent/graft assembly 10 inverted relative to the preferred and eventual orientation. Thus, the tubular graft 12 may initially be in an upstream position, and accordingly may collapse somewhat during the initial stages of the insertion. However, the tubular graft 12 of the stent/graft assembly will move into the downstream position relative to the tubular stent 20 as the stent/graft assembly 10 moves into the left iliac artery 44. Thus, any collapsing of the more flexible graft 12 that may have occurred during initial insertion through the right iliac artery 40 will be offset by the above-described wind-sock effect as the stent/graft assembly 10 moves into the left iliac artery 44.

Figure 10:
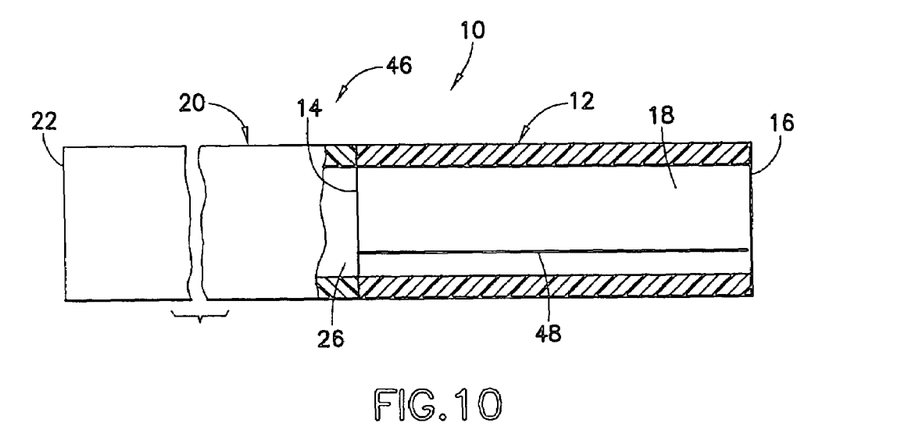
FIG. 10 is an elevational view, partly in section of a third alternate endovascular stent/graft assembly.

In certain instances, it may be desirable to provide support for the tubular graft 12 of the stent/graft assembly 10. For example, a third embodiment of the endovascular stent/graft assembly is identified generally by the numeral 46 in FIG. 10. The endovascular stent/graft assembly 46 includes a tubular graft 12 with an upstream end 14, a downstream end 16 and a tubular passage therebetween, substantially as in the first and second embodiments. The stent/graft assembly 46 further includes a tubular stent 20 having an upstream end 22, a downstream end 24 and a tubular passage 26 extending between the ends. As in the first embodiment, the upstream end 14 of the tubular graft 12 is affixed in substantially end-to-end relationship with the downstream end 24 of the tubular stent 20. The endovascular stent/graft assembly 46 differs from the first embodiment by the inclusion of a single wire 48 extending from the tubular stent 20 axially along the tubular graft 12 and affixed to the tubular graft 12 in proximity to downstream end 16. The wire 48 ensures that the tubular graft 12 will remain substantially in an extended condition and will prevent the downstream end 16 of the tubular graft 12 from collapsing toward the tubular stent 20. The provision of the wire 48 may be helpful, for example, in instances depicted in FIG. 9 where an endovascular stent/graft assembly may travel in counter flow direction with the tubular graft 12 in an upstream position relative to the tubular stent 20. Thus, the wire 48 allows the assembly 46 to be deployed with the tubular stent 20 downstream of the tubular graft 12 when there is no upstream landing place for the tubular stent 20. A second internal stent, such as the internal stent 27 of FIG. 1, then is deployed to open the tubular graft 12. In this embodiment, the wind sock effect does not occur.

Figure 11:
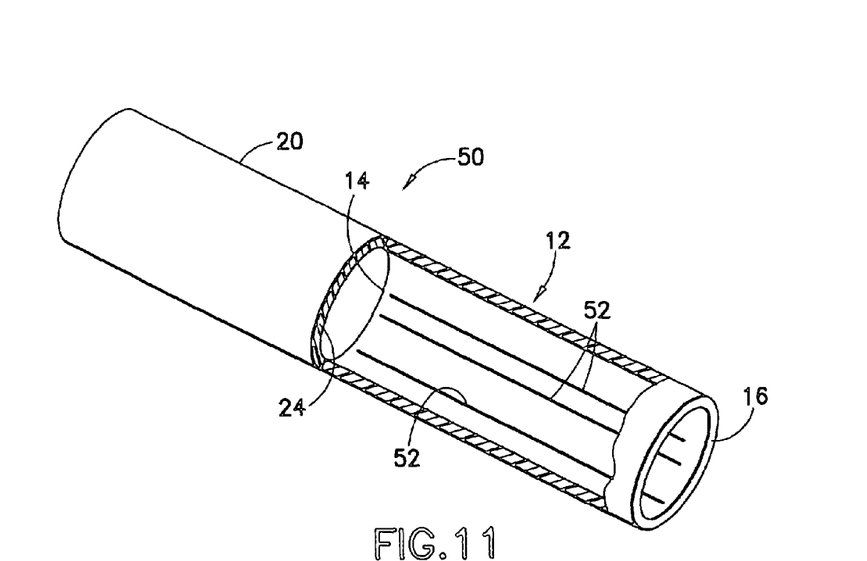
FIG. 11 is a perspective view of a fourth embodiment of an endovascular stent/graft assembly in accordance with the subject invention.

A fourth embodiment of the endovascular stent/graft assembly is identified by the numeral 50 in FIG. 11. The endovascular stent/graft assembly 50 is a variation of the stent/graft assembly 46 of FIG. 10 in that a plurality of wires 52 extend axially from the stent 20 substantially to the downstream end 16 of the tubular graft 12 where the wires 52 are affixed to the tubular graft 12. The stent/graft assembly 50 prevents axial collapsing of the tubular stent 20, substantially as with the embodiment of FIG. 10. However, the wires 52 will further provide radially support for the tubular graft 12 and will resist radially collapsing of the graft 12.

Figure 12:
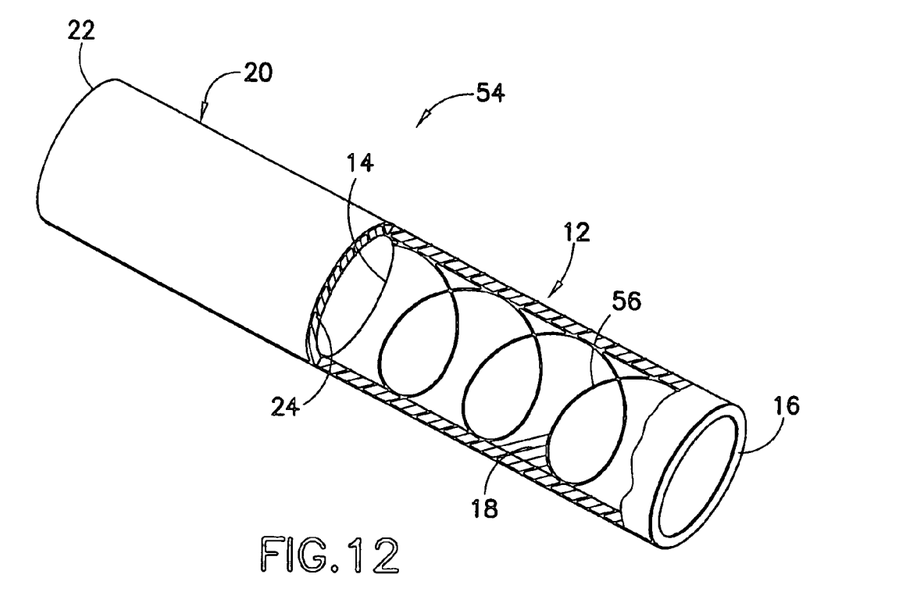
FIG. 12 is a perspective view of an endovascular stent/graft assembly in accordance with a fifth embodiment of the subject invention.
Figure 13:
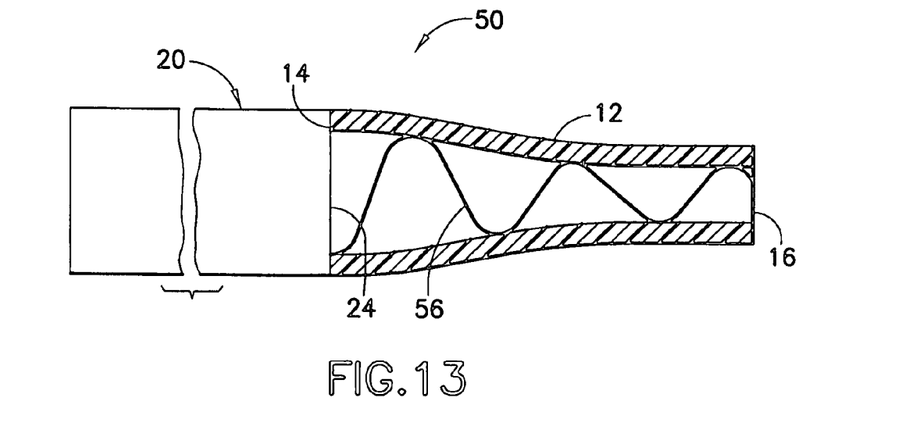
FIG. 13 is a side elevational view of the endovascular stent/graft assembly of FIG. 12 with a cross-sectional variation along the length of the graft to accommodate cross-sectional variations of the blood vessel.

A fourth embodiment of the endovascular stent/graft assembly is identified by the numeral 54 in FIGS. 12 and 13. The stent/graft assembly 54 is similar to the stent/graft assemblies of FIGS. 10 and 11. However, the axially aligned wires of the previous embodiment are replaced with a coil 56. The coil 56 may be anchored to the tubular stent 20 or to the upstream end 14 of the tubular graft 12 for affixation to the downstream end 16 of the tubular graft 12. The coil 56 resists axially collapsing and will assist with axial extension in response to any axial collapse that does occur. Additionally, the coil 56 provides greater outwardly directed radially forces on the tubular graft 12 then either of the previous embodiments.

Figure 14:
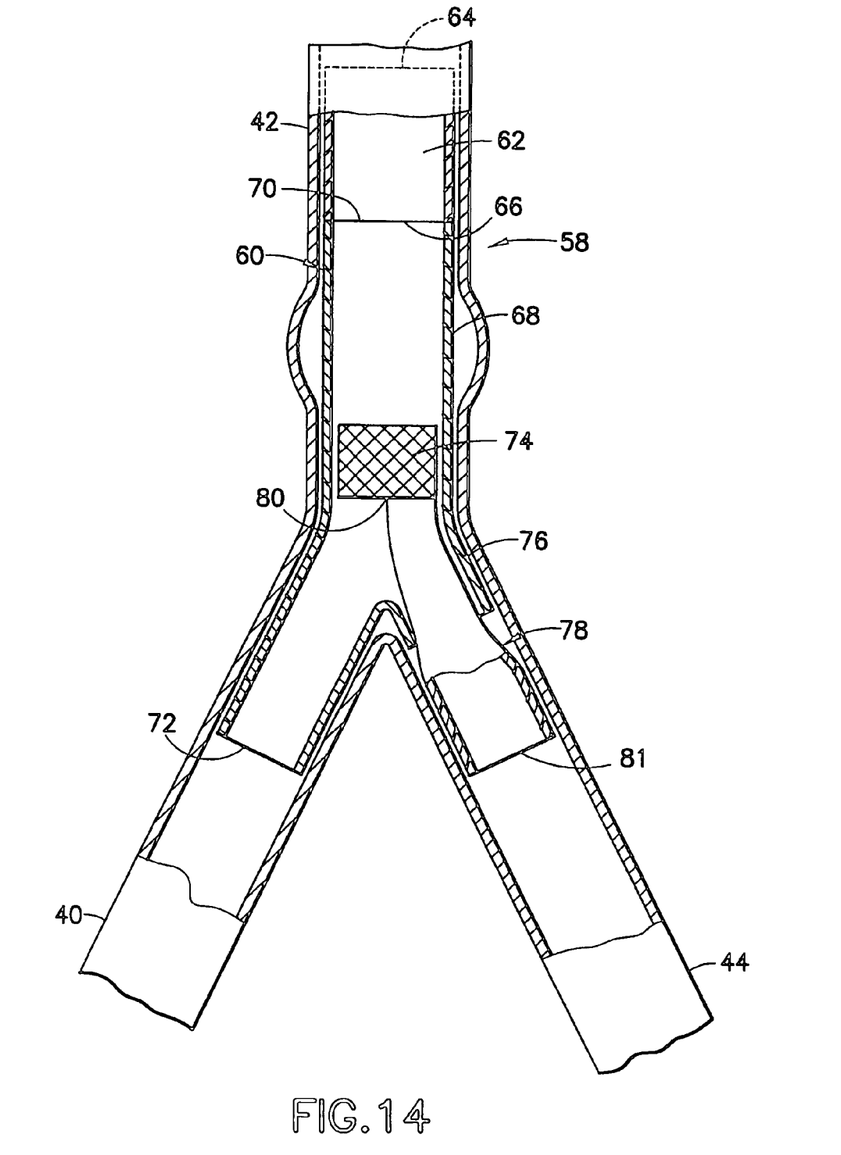
FIG. 14 is a schematic view of a modular endovascular stent/graft assembly that represents a sixth embodiment of the invention intended primarily for deployment into the abdominal aorta and adjacent regions of the left and right iliac arteries.

The endovascular stent/graft assembly 32 of FIG. 6 shows that a plurality of stents 20, 34 can be assembled with a single tubular graft 12. The principles embodied in FIG. 6 can be employed further to develop more complex modular assemblies. For example, FIG. 14 shows a modular assembly for repairing vascular anomalies in the region where the abdominal aorta 42 meets the right iliac artery 40 and the left iliac artery 44. In particular, the modular endovascular stent/graft assembly 58 comprises a first modular subassembly 60 with a first tubular stent 62 with an upstream end 64 and an opposed downstream end 66. The first modular subassembly 60 further comprises a first tubular graft 68 with an upstream end 70 connected substantially in end-to-end axial relationship with the downstream end 66 of the first stent 62. The first tubular graft 68 further includes a downstream end 72. The first modular component 60 is deployed from a right leg approach into the right iliac artery 40. The first tubular stent 62 then is advanced sufficiently into the abdominal aorta 42 for the first tubular stent 62 to be upstream of the aneurysm or other vascular abnormality in the abdominal aorta 42.

The modular assembly 60 further includes a second tubular stent 74 that is mounted unrestrained in the first tubular graft 68 at a location downstream from or within the aneurysm. The first tubular graft 68 further includes tubular exit 76 at a location between the second tubular stent 74 and the downstream end 72 of the first tubular graft. The second tubular stent 74 preferably is cross-sectionally larger than both the exit 76 and portions of the first tubular graft 68 in proximity to the exit 70. Thus, the unrestrained second tubular stent 74 will not slip longitudinally into either the exit 76 or downstream portions of the first tubular graft 68.

The assembly 58 further includes a second tubular graft 78 with an upstream end 80 and a downstream end 81. The second tubular graft 78 is deployed from a left leg approach into the left iliac artery 44 and is advanced through the exit 76 of the first tubular graft 68. The upstream end 80 of the second tubular graft 78 is connected substantially end-to-end with the second tubular stent 74. Internal stents then may be inserted, such as the internal stent 27 described with respect to the first embodiment.

Figure 15:
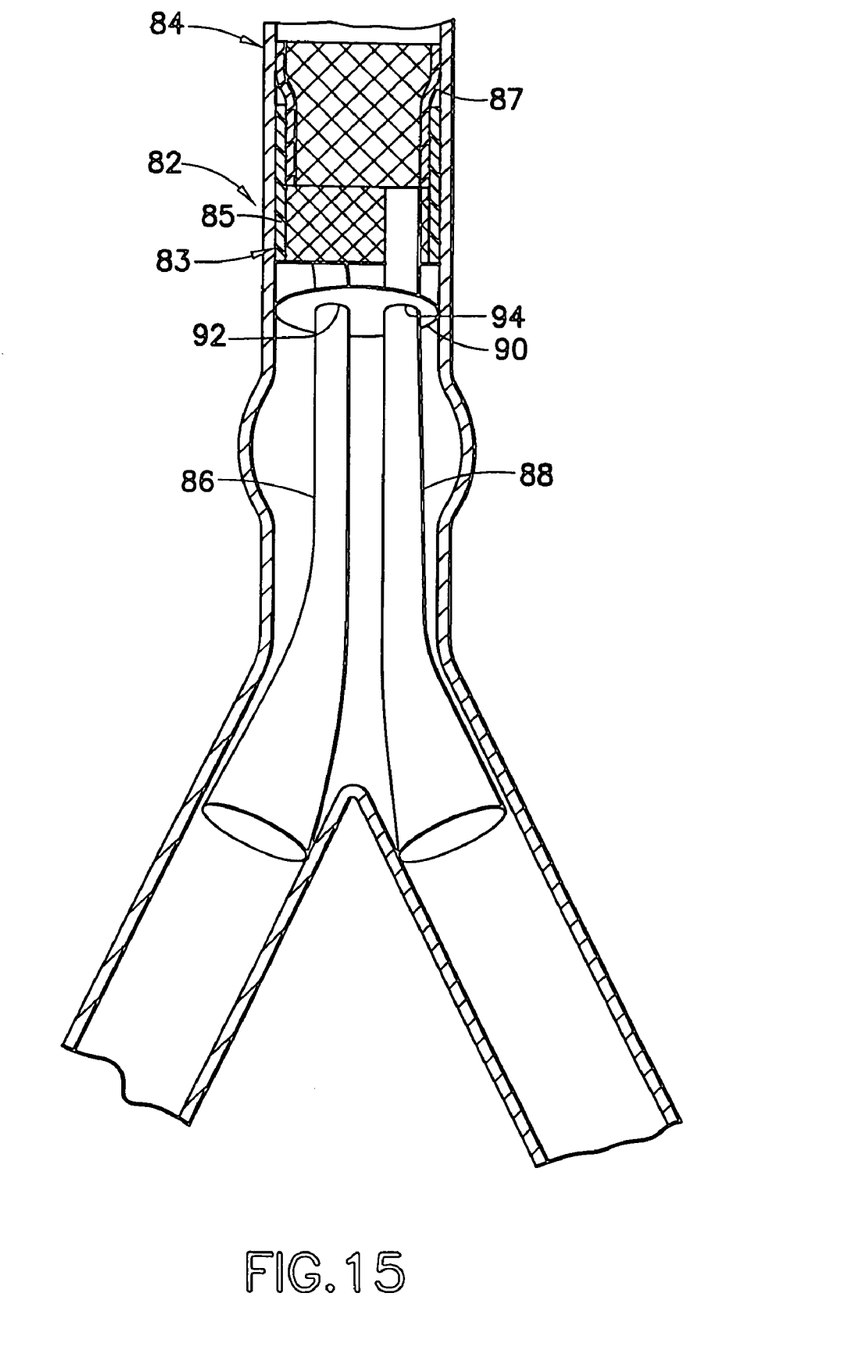
FIG. 15 is a schematic view of a seventh embodiment of an endovascular stent/graft assembly in accordance with the invention.

A seventh embodiment of the endovascular stent/graft assembly of the subject invention is identified generally by the numeral 82 in FIG. 15. The assembly 82 comprises first and second endovascular stent/graft subassemblies 83 and 84. The first subassembly 83 comprises a first stent 85 and a first tubular graft 86. Similarly, the second subassembly 84 comprises a second stent 87 and a second graft 88. The assembly 82 further includes a generally disc-like drum secured in the abdominal aorta 42 at a location upstream of the aneurysm. The drum 90 has first and second mounting apertures 92 and 94 through which portions of the first and second tubular grafts 86 and 88 extend. The extreme upstream ends of the tubular grafts 86 and 88 are secured respectively in end-to-end relationship with the downstream end of the first and second tubular stents 85 and 87, while the downstream ends of the tubular grafts 86 and 88 are disposed respectively in the right and left iliac arteries 40 and 44. The drum or disc 90 prevents blood from flowing around the tubular grafts 86 and 88 and into the region of the aneurysm where blood pressure could cause a rupture of the aneurysm. The stents 85 and 87 provide a secure mounting of the endovascular stent/graft assembly 82 relative to the aneurysm, and prevent any parts of the assembly 82 from migrating downstream due to the pressure of the blood flow. The endovascular stent/graft assembly 82 of FIG. 15 is used in combination with internal stents, such as the internal stent 27 in FIG. 1, that are introduced to the tubular grafts 86 and 88 after complete implantation of portions of the assembly 82 depicted in FIG. 15. Additionally, the assembly 82 may be used in combination with one or two downstream stents, or other fixation devices secured to downstream ends of the respective tubular grafts 86 and 88.

Figure 16:
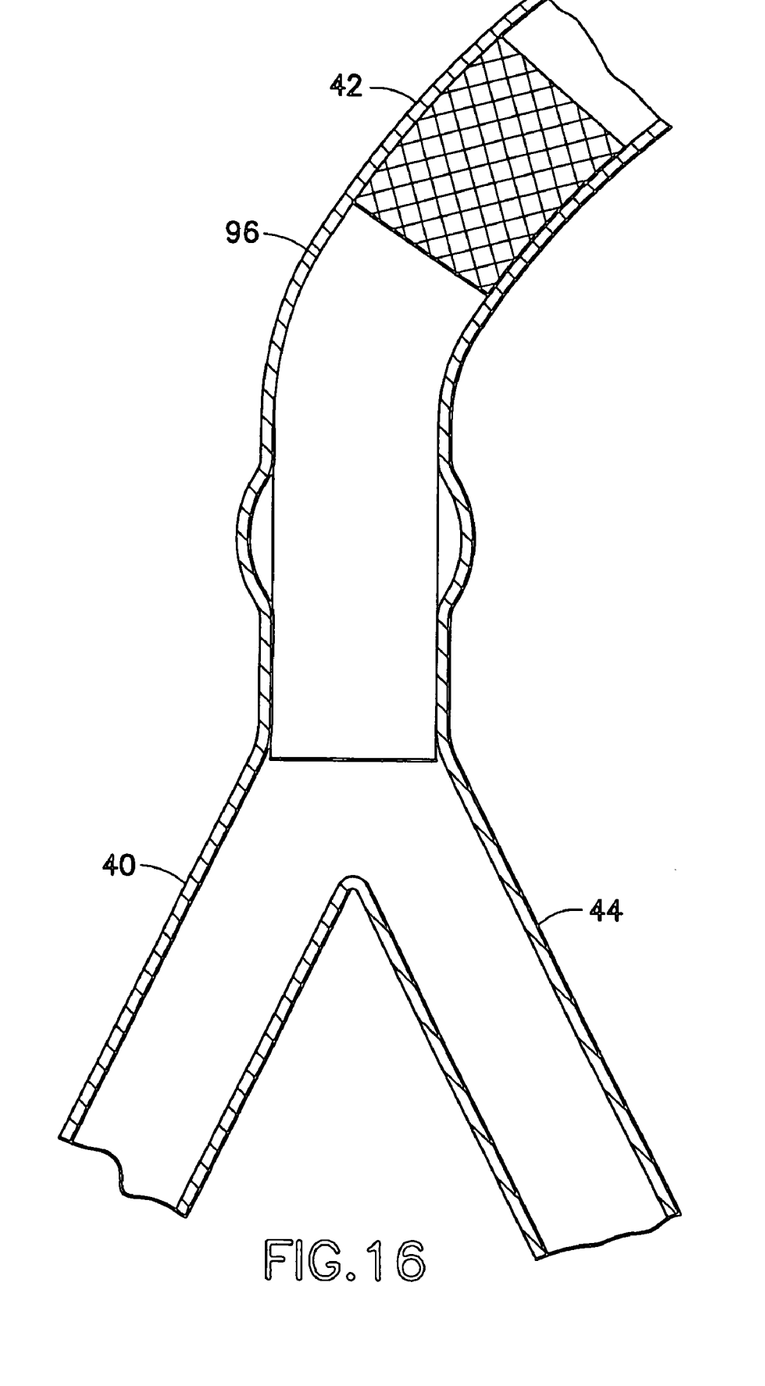
FIG. 16 is a schematic view of an eighth embodiment of an endovascular stent/graft assembly in accordance with the invention.

An eighth embodiment of the endovascular stent/graft assembly of the subject invention is identified generally by the numeral 96 in FIG. 16. The stent/graft assembly 96 is designed in recognition of the fact that somewhat less than half of all patients have a neck defined in the abdominal aorta immediately upstream of the aneurysm. The neck is aligned to the aneurysm at an angle of less than 180°. Although endovascular grafts exhibit some flexibility, it can be cumbersome to advance an initially linear endovascular stent/graft assembly through the aneurysm and through the angularly aligned portions of the aneurysm and neck of the abdominal aorta 42. To avoid this difficulty, the endovascular stent/graft assembly 96 of FIG. 16 is preformed to exhibit a curve between the upstream and downstream ends. The curved endovascular stent/graft assembly 96 is better suited for deployment and fixation into regions of the abdominal aorta 42 that have the angulated neck of FIG. 16.

Figure 17:
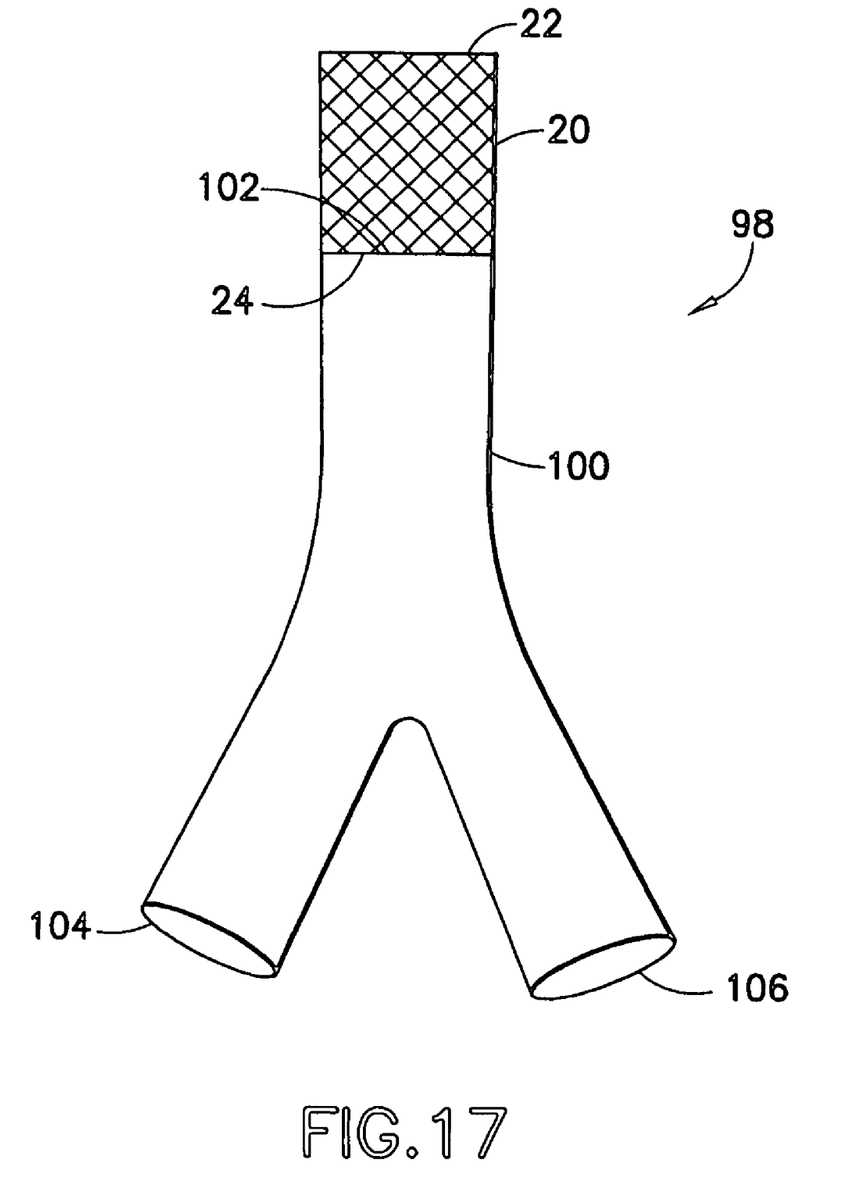
FIG. 17 is a schematic view of a modular endovascular stent/graft assembly that represents a ninth embodiment of the invention intended primarily for deployment into the abdominal aorta and adjacent regions of the left and right iliac arteries.

FIG. 17 shows an endovascular stent/graft assembly 98 with a stent 20, substantially identical to the stents 20 described and illustrated above. More particularly, the stent 20 of the assembly 98 in FIG. 17 has opposed upstream and downstream ends 22 and 24. The assembly 98 includes a one piece bifurcated graft 100. The graft 100 includes an upstream end 102 that is fixed in substantially end-to-end axial engagement with the downstream end 24 of the stent 20. Additionally, the graft 100 includes two downstream legs 104 and 106 for disposition respectively in the right and left iliac arteries 40 and 44. The one piece bifurcated graft 100 of FIG. 17 eliminates some of the intraoperative assembly required with the modular system of FIG. 14. The bifurcated graft 100 is used with one or more internal stents that are deployed after insertion substantially as described with respect to the other embodiments. Additionally, downstream stents can be affixed to either of the downstream legs 104 and 106.

Variations of the FIG. 17 embodiment also may be provided. For example, more than two legs may be provided. Furthermore the stent 20 may have branches intermediate its length, and tubular grafts may be connected in substantially end-to-end relationship with the branches of the stent.

Figure 18:
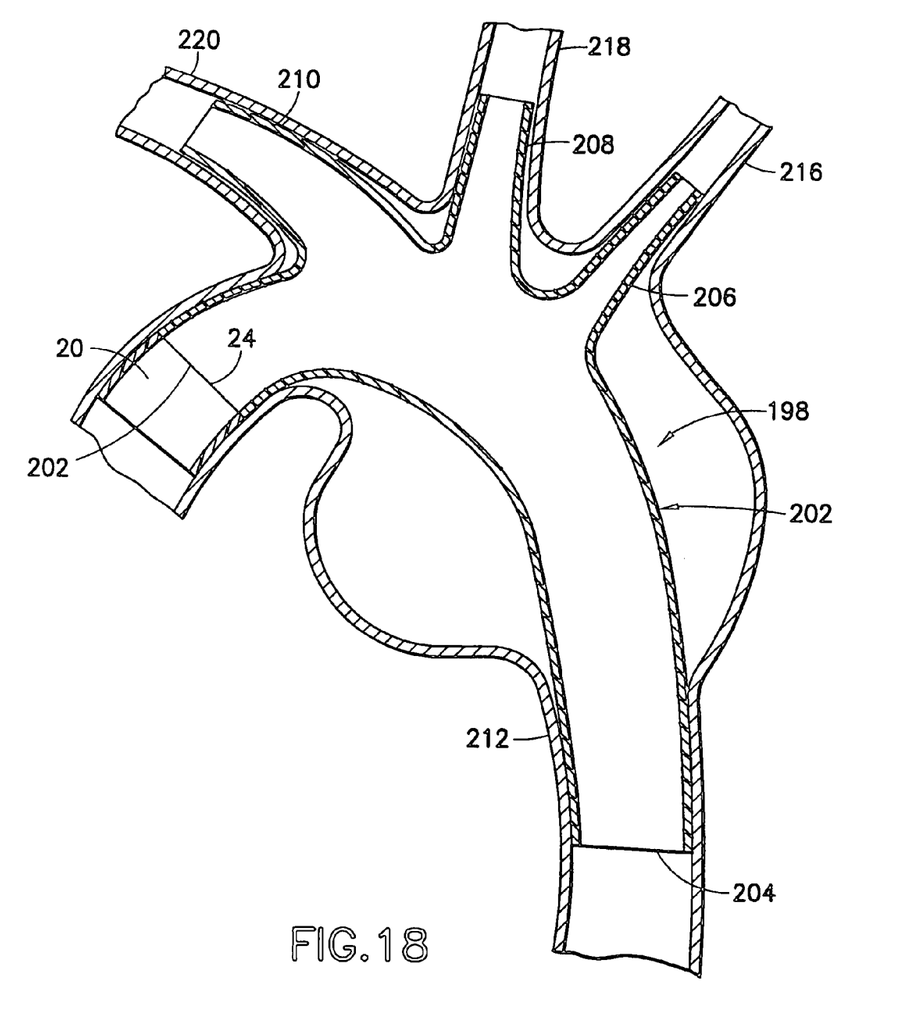
FIG. 18 is a schematic view of a variation of the stent/graft assembly of FIG. 17.

An example of a variation of the FIG. 17 embodiment is illustrated in FIG. 18. In particular, FIG. 18 shows an endovascular stent/graft assembly 198 with a stent 20 identical to the stent 20 described and illustrated above. The assembly 198 includes a graft 200 with a tubular upstream end 202 connected to the downstream end 24 of the stent 20. The graft 200 also has a tubular downstream end 204 and three tubular branches 206, 208 and 210 extending transversely from intermediate positions along the graft 200. FIG. 18 shows the endovascular stent/graft assembly 198 deployed for treating an aneurysm of the thoracic aorta 212. The tubular branches 206, 208 and 210 extend to arteries that branch from the thoracic aorta 212, including the left subclavian artery 216, the left carotid artery 218 and the brachiocephalic artery 220.

Figure 19:
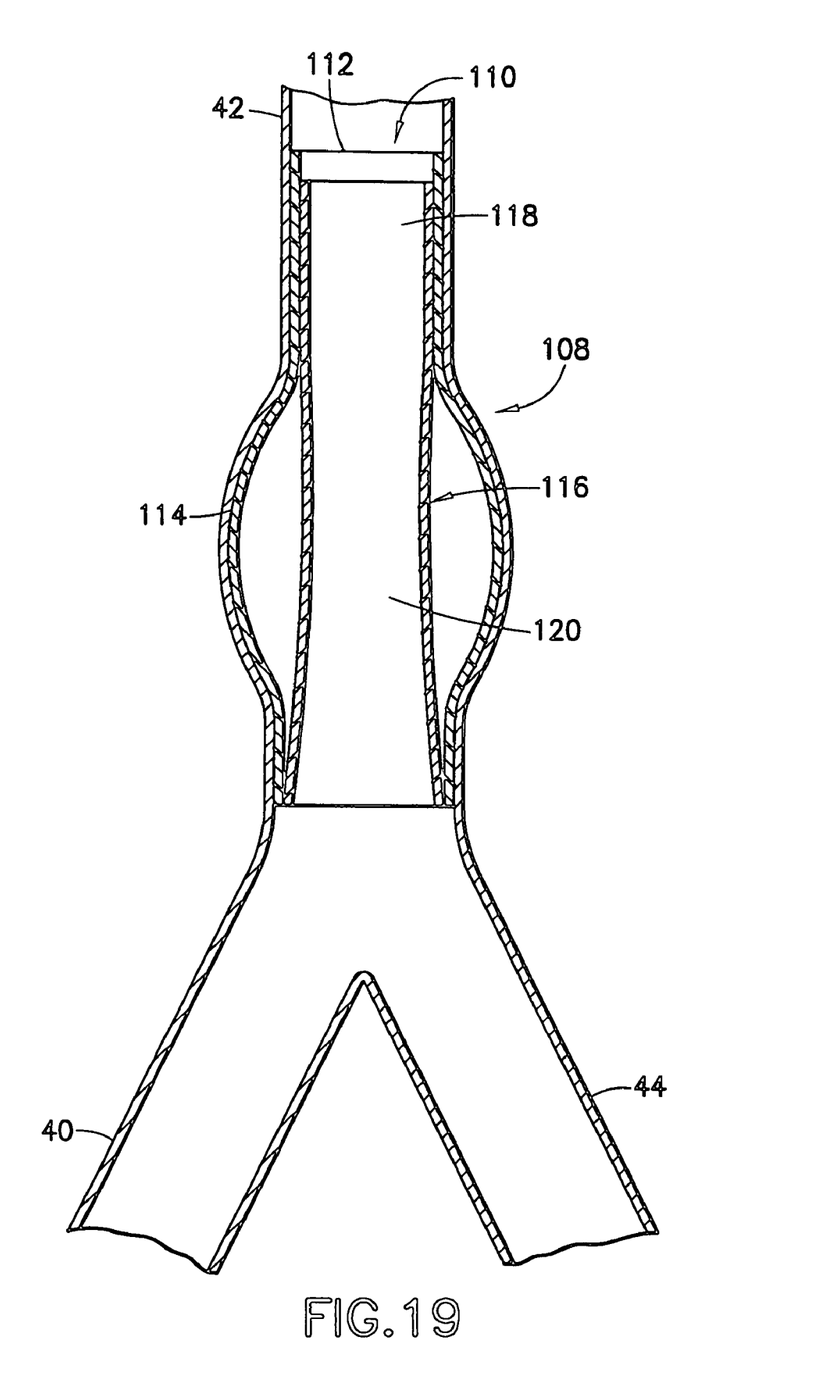
FIG. 19 is a schematic view of a tenth embodiment of an endovascular stent/graft assembly in accordance with the invention.

In many instances, small blood vessels will communicate with portions of the abdominal aorta that have the aneurysm. Blood delivered by these blood vessels can increase pressure between the aneurysm and the graft. Such pressure can lead to a rupture of the aneurysm and/or damage to the graft. The endovascular graft assembly 108 of FIG. 19 is specifically configured to occlude small side blood vessels that lead into the aneurysm. More particularly, the assembly 108 includes an outer stent/graft subassembly 110 that comprises an upstream tubular stent 112 and a downstream expandable graft 114. The stent 112 and graft 114 are connected in substantially end-to-end axial alignment as described and illustrated with respect to the other embodiments herein. The downstream graft 114 of the outer stent/graft subassembly 110 differs from the tubular grafts described and illustrated above. More particularly, the outer graft 114 may be a synthetic fabric or a detachable balloon that has been used in the prior art. Specifically, the outer graft 114 can be expanded radially to conform substantially to the shape of the aneurysm and to thereby occlude the small blood vessels that lead into the aneurysm. The assembly 108 further includes an inner stent/graft subassembly 116 that has an upstream stent 118 and a downstream tubular graft 120. The inner subassembly 116 may be substantially identical to the endovascular stent/graft assembly 10 described with respect to FIG. 1 and other embodiments set forth above. Thus, the tubular graft 120 of the inner subassembly 116 is not expandable. An inner stent similar to the inner stent 27 described and illustrated above may extend through the tubular graft 120. The space between the inner and outer graft 114 and 120 may be filled with blood, a contrast liquid, an adhesive or water. Variations of this embodiment may include a detachable balloon between the inner graft 120 and the expandable outer graft 114. Alternatively, the detachable balloon may make the separate inner graft unnecessary. Still further, the detachable balloon may make a separate internal stent for the outer graft unnecessary.

While the invention has been described with respect to certain preferred embodiments, it is apparent that various changes can be made without departing from the scope of the invention as defined by the appended claims. For example, for each of the optional embodiments, and variations thereof, the substantially end-to-end stent-to-graft connections can be pure end-to-end abutment as depicted schematically in FIG. 2 or a slightly overlapped telescoped arrangement, as shown in FIG. 3. In other options, there may be a greater telescoping between the graft and stent prior to deployment and/or during deployment. However, the graft and stent then may be extended intraoperatively into the slightly overlapped relationship depicted in FIG. 3.

What is claimed is:

1. An endovascular stent/graft assembly for repairing a section of a blood vessel that has an aneurysm, said blood vessel having first and second relatively healthy sections adjacent and on opposite ends of said aneurysm, said assembly comprising:

a substantially tubular stent means for directly contacting said first relatively healthy section of said blood vessel, said stent means having opposite first and second axial ends; and a substantially tubular graft means for directly contacting said first and second relatively healthy sections of said blood vessel and for bridging said aneurysm, said graft means having a first axial end, portions of said graft means adjacent said first axial end being for directly contacting said first relatively healthy section of said blood vessel, said first axial end of the graft means being fixedly connected with the second axial end of the stent means for achieving an end-to-end connection without overlap, said graft means further having a second axial end for directly contacting said second relatively healthy section of said blood vessel, such that portions of said graft means between said first and second axial ends bridge said aneurysm of said blood vessel, whereby the end-to-end connection without overlap enables a smaller cross-section than a connection with overlap so that the endovascular stent/graft assembly can be introduced more easily into the blood vessel.

2. The endovascular stent/graft assembly of claim 1 wherein the first axial end of the tubular graft means and the second axial end of the stent means are affixed by bonding.

* * * * *